United States Patent [19]

Vedamuthu et al.

[11] Patent Number: 5,348,881
[45] Date of Patent: Sep. 20, 1994

[54] MULTIPLE BACTERIOCIN PRODUCING LACTOCOCCUS AND COMPOSITIONS

[75] Inventors: Ebenezer R. Vedamuthu; James T. Henderson, both of Bradenton; Peter A. Vandenbergh, Sarasota, all of Fla.

[73] Assignee: Quest International Flavors & Good Ingredients Company, division of Indopco, Inc., Bridgewater, N.J.

[21] Appl. No.: 880,003

[22] Filed: May 8, 1992

Related U.S. Application Data

[63] Continuation-in-part of Ser. No. 840,503, Feb. 24, 1992, which is a continuation-in-part of Ser. No. 492,969, Mar. 13, 1990, abandoned, and Ser. No. 721,774, Jul. 1, 1991, Pat. No. 5,173,297.

[51] Int. Cl.$^5$ ............................................. C12N 1/12
[52] U.S. Cl. ........................... 435/252.1; 435/252.4; 435/71.3; 435/822; 424/93.3; 424/93.4; 426/61
[58] Field of Search ................. 435/71.3, 252.1, 252.3, 435/885, 822; 424/93 D, 93 C; 426/61

[56] References Cited

U.S. PATENT DOCUMENTS

| | | | |
|---|---|---|---|
| 4,477,471 | 10/1984 | Gonzalez | 435/885 |
| 4,599,313 | 7/1986 | Gonzalez | 435/885 |
| 4,716,115 | 12/1987 | Gonzalez | 435/885 |
| 4,728,516 | 3/1988 | Boudreaux | 435/885 |
| 4,740,593 | 4/1988 | Gonzalez | 435/885 |
| 4,871,539 | 10/1989 | Hata | 435/885 |
| 4,918,014 | 4/1990 | Vedamuthu | 935/72 |
| 4,956,177 | 9/1990 | King et al. | 424/93 |
| 5,066,588 | 11/1991 | Vadamuthu | 435/172.3 |
| 5,139,950 | 8/1992 | Klaenhammer | 435/252.3 |
| 5,218,101 | 6/1993 | Hansen | 536/23.7 |

OTHER PUBLICATIONS

Schleifer, K. H., FEMS Microbiol. Rev. 46 (3): 201–203 (1987).
Klaenhammer, T. R., Biochimie 70 (3): 337–349 (1988).
Delves-Broughton., Food Technol. 44 (11) 100–112, 117 (1990).
Gilliland, S. E., Bacterial Starter Cultures for Foods. CRC Press Inc., Boca Raton, Fla. pp. 5 to 23, (1985).
Gonzalez, C. F. et al, Appl. Environ. Microbiol. 46:81–89 (1983).
Gonzalez, C. F. et al, Appl. Environ. Microbiol. 53:2534–2538 (1987).
Geis, A, "Potential of Lactic Strepotococci to Produce Bacteriocini", *Applied and Environmental Microbiology*, vol. 45, No. 1, pp. 205–211, 1983.

*Primary Examiner*—Marian Knode
*Attorney, Agent, or Firm*—Ian C. McLeod

[57] ABSTRACT

A group N Lactococcus which produces two or more bacteriocins from different Lactococcus are described. *Lactococcus lactis* subspecies *lactis* 18922 with DNA encoding two bacteriocins from different Lactococcus is particularly disclosed for use in foods to inhibit *Lactobacillus casei* and other food contaminants. Bacteriocin containing compositions, bacterial mixtures and method of use in foods are also described.

2 Claims, 1 Drawing Sheet

CONJUGATIVE TRANSFER OF pSRQ400

MATING EXPERIMENTS: AGAR SURFACE MATING PROCEDURE WAS USED

| DONOR | | RECIPIENT |
|---|---|---|
| LLA 2.0 | | (LLA 1.2 |
| (Lac$^+$, LL-2$^+$ | | (Lac$^-$, LL-2$^-$; |
| Str$^s$, Fus$^s$, LL-1$^-$) | | Str$^r$  Fs$^r$, LL-1$^+$) |

1:2
1:4

0.2 ml/plate — 0.2 ml/plate — 0.2 ml/plates
5 plates (BMG) — 5 plates (BMG) — 5 plates (BMG)

INCUBATE OVERNIGHT IN BBL-GAS PAK JAR AT 32°C

HARVEST CELL BY WASHING WITH 2.0ml PO$_4$ BUFFER/PLATE

FOR EACH SET CENTRIFUGE, WASH, AND RESUSPEND CELLS IN 1.1ml PO$_4$

SPREAD 0.2ml/PLATE OF SAMPLE (5 PLATES PER SET)
BML-(BCP)-Str$^{1000}$
INCUBATE 48HR. AT 32°C IN GAS-PAK JAR AND EXAMINE

FIG. 1

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 34
        ( B ) TYPE: Amino Acid
        ( C ) STRANDEDNESS: Single
        ( D ) TOPOLOGY: Linear ( i i ) MOLECULE TYPE:
        ( A ) DESCRIPTION: Peptide ( i i i ) HYPOTHETICAL: No ( i v ) ANTI-SENSE: No ( v ) FRAGMENT TYPE: N/A ( v i ) ORIGINAL SOURCE:
        ( A ) ORGANISM: Lactococcus lactis
        ( B ) STRAIN:
        ( C ) INDIVIDUAL ISOLATE: LLA 2.0
        ( D ) DEVELOPMENTAL STAGE: N/A
        ( E ) HAPLOTYPE: N/A
        ( F ) TISSUE TYPE: N/A
        ( G ) CELL TYPE: N/A
        ( H ) CELL LINE: N/A
        ( I ) ORGANELLE: N/A ( v i i ) IMMEDIATE SOURCE:

( v i i i ) POSITION IN GENOME: N/A ( i x ) FEATURE:

(A) NAME/KEY: bacteriocin
(B) LOCATION: N/A
(C) IDENTIFICATION METHOD: sequencing
(D) OTHER INFORMATION: Bacteriocin produced by
    strain (x) PUBLICATION INFORMATION: N/A (xi) SEQUENCE DESCRIPTION: SEQ ID NO: 1:

```
Ile Thr Ser Ile Ser Leu Cys Thr Pro Gly Cys Lys Thr Gly
 5               10
Ala Leu Met Gly Cys Asn Met Lys Thr Ala Thr Cys Asn Cys
15               20                       25
Ser Ile His Val Ser Lys
30
```

MULTIPLE BACTERIOCIN PRODUCING LACTOCOCCUS AND COMPOSITIONS

CROSS-REFERENCE TO RELATED APPLICATIONS

The present application is a continuation-in-part of U.S. application Ser. No. 07/840,503, filed Feb. 24, 1992, which is a continuation-in-part of Ser. No. 07/492,969, filed Mar. 13, 1990, now abandoned, and application Ser. No. 07/721,774, filed Jul. 1, 1991 now U.S. Pat. No. 5,173,297.

BACKGROUND OF THE INVENTION

(1) Field of the Invention

The present invention relates to Lactococcus which produce at least two bacteriocins and to compositions incorporating the bacteriocins. In particular, the present invention relates to Lactococcus which contain DNA transferred from a donor Lactococcus which provides a bacteriocin along with a bacteriocin from a recipient Lactococcus strain.

(2) Prior Art

The genus Lactococcus includes dairy lactic streptococci that belong to the Lancefield serological group N. The species involved are *Lactococcus lactis* subsp. *lactis*, *Lactococcus lactis* subsp. *cremoris*, and citrate-fermenting *Lactococcus lactis* subsp. *lactis* biovar *diacetylactis* (Schleifer, K. H., FEMS Microbiol. Rev. 46(3):201–203 (1987)). The aforementioned species are traditionally used in dairy fermentations and are "generally regarded as safe" (GRAS) by the United States Department of Agriculture.

Certain strains of group N Lactococcus spp. produce proteinaceous antagonistic substances against closely related bacteria called bacteriocins (Klaenhammer, T. R., Biochimie 60(3):337–349 (1988)). Most of these bacteriocins have a narrow spectrum of activity either antagonistic to other strains within the species or to certain strains in closely related species. Nisin, a bacteriocin produced by certain strains of *Lactococcus lactis* subsp. *lactis*, however, has a wider spectrum of activity affecting other Gram-positive bacteria including the spore-forming Clostridia and Bacillus spp. (Delves-Broughton., Food Technol. 44(11):100–112, 117 (1990)).

Because of the traditional use of the dairy lactococci in various food fermentations (Gilliland, S. E., Bacterial Starter Cultures for Foods. CRC Press Inc., Boca Raton, Fla. pages 5 to 23, (1985)), their GRAS status and their non-pathogenicity, bacteriocins produced by these bacteria can be safely used in food systems (either produced in situ in the food system by adding the live cultures or added to food systems as cell-free purified or semi-purified or crude preparations) to extend the shelf life or to provide a margin of safety against potential food-borne pathogens. The utility of such bacteriocin-producing strains could be particularly increased if the bacteriocin-producing potential of the strains is broadened by introducing into such strains genetic information for different types of bacteriocins from closely related strains or species.

A transfer of genetic information can be achieved by conjugation, transformation (including electrotransformation), and transduction. The problem is generally, that the bacteriocins are antagonistic to the recipient Lactococcus and the recipients are either killed or the transfer does not take place.

OBJECTS

It is therefore an object of the present invention to provide Lactococcus strains which encode at least two bacteriocins and which are useful in food fermentations. Further, it is an object of the present invention to provide compositions and a method of use incorporating the bacteriocins. Further still, it is an object of the present invention to provide compositions which are safe and economical. These and other objects will become increasingly apparent by reference to the following description and the drawings.

IN THE DRAWINGS

FIG. 1 is a schematic diagram showing the steps in mating of plasmid pSRQ400 into a recipient Lactococcus strain which is preferred.

GENERAL DESCRIPTION

The present invention relates to a group N Lactococcus sp. selected from the group consisting of *Lactococcus lactis*, *Lactococcus cremoris* and *Lactococcus lactis* biovar *diacetylactis* and containing DNA from *Lactococcus lactis* NRRL-B-18809 (LLA 2.0) encoding a bacteriocin, wherein the Lactococcus sp. encodes the bacteriocin from the *Lactococcus lactis* NRRL-B-18809 along with a different bacteriocin from a strain which is a parent to the Lactococcus sp.

In particular, the present invention relates to a method for preserving a food against *Lactobacillus casei* growth present as a contaminant in the food which comprises: providing in the food cells of a group N Lactococcus sp. selected from the group consisting of *Lactococcus lactis*, *Lactococcus cremoris* and *Lactococcus lactis* biovar *diacetylactis* and containing DNA from *Lactococcus lactis* NRRL-B-18809 encoding a bacteriocin, wherein the Lactococcus sp. encodes the bacteriocin from the *Lactococcus lactis* NRRL-B-18809 along with a different bacteriocin from a strain which is a parent to the Lactococcus sp., wherein the Lactococcus sp. strain is provided in the food and wherein the cell numbers are sufficient to inhibit *Lactobacillus casei*.

Further still, the present invention relates to a composition which comprises in admixture (A) a first bacteriocin produced by *Lactococcus lactis* NRRL-B-18809 and (B) a second bacteriocin produced by Lactococcus NRRL-B-18535, wherein the ratio by weight of (A) to (B) is between about 25 to 1 and 1 to 25, and wherein the composition inhibits *Lactobacillus casei* and other bacteria which can be present as contaminants in a food.

The present invention also relates to a method for preserving a food against growth of *Lactobacillus casei* and other bacteria which can be present as contaminants which comprises providing a composition which comprises in admixture (A) a first bacteriocin produced by *Lactococcus lactis* NRRL-B-18809 and (B) a second bacteriocin produced by Lactococcus NRRL-B-18535, in amounts sufficient to inhibit the *Lactobacillus casei* and the other bacteria present as contaminants in the food.

The present invention further relates to a method for preserving a food against *Lactobacillus bulgaricus* growth present as a contaminant in the food which comprises providing in the food cells of a *Lactococcus lactis* which produces a nisin-like bacteriocin and cells of *Lactococcus lactis* NRRL-B-18809 in an amount sufficient to inhibit the *Lactobacillus casei*.

Finally the present invention relates to a bacterial composition which comprises (A) cells of a *Lactococcus lactis* which produces a nisin-like bacteriocin and (B) cells of *Lactococcus lactis* NRRL-B-18809 in an amount sufficient to inhibit a *Lactobacillus casei* and other contaminant bacteria in a food.

The donor strain is *Lactococcus lactis* NRRL-B-18809, also known as LLA 2.0, which produces a unique bacteriocin. The strain contains plasmid pSRQ400 which encodes the bacteriocin. The preferred recipient strain is *Lactococcus lactis* NRRL-B-18535, also known as LLA 1.2, which produces a nisin-like bacteriocin. The preferred transconjugant strain is *Lactococcus lactis* NRRL-B-18922. These strains are on deposit with the Northern Regional Research Laboratory in Peoria, Ill. under the Budapest Treaty. Other strains which can be used as recipients are *Lactococcus cremoris* and *Lactococcus lactis* biovar *diacetylactis* which produce a bacteriocin, although they are not preferred.

The bacteriocin produced by *Lactococcus lactis* NRRL-B-18809, as the donor strain (LLA 2.0), has the formula Ile Thr Ser Ile Ser Leu Cys Thr Pro Gly Cys Lys Thr Gly Ala Leu Met Gly Cys Asn Met Lys Thr Ala Thr Cys Asn Cys Ser Ile His Val Ser Lys.

The strain LLA 2.0 is described in detail in U.S. application Ser. No. 07/721,774. It produces a unique bacteriocin. The bacteriocin produced by *Lactococcus lactis* NRRL-B-18535 as a recipient strain is nisin-like, although differing from nisin in one amino acid. This bacteriocin is described in detail in U.S. application Ser. No. 07/492,969. The exact chemical and physical structure of this bacteriocin is uncertain.

The bacteriocins are provided together in foods. They can be provided by using a single transconjugant strain producing both bacteriocins or by two strains producing the bacteriocins individually. The Lactococcus sp. can also be combined together and introduced into the food.

The Lactococcus are grown in a conventional growth media to express the bacteriocin(s) and can be frozen or lyophilized. The bacteriocin(s) can be isolated from the growth media and used in the food. They can also be preserved in lyophilized or frozen form for shipment prior to use.

Where the bacteriocins are to be produced, the preferred media are those described in application Ser. Nos. 07/492,969 and 07/721,774 for *Lactococcus lactis* NRRL-B-18809 and NRRL-B-18535. The most preferred media was MRS Lactobacillus Broth (Difco, Detroit Mich.). The bacteriocin was isolated from the growth media and can be concentrated as described in these applications using ultrafiltration and the like.

The mixture of bacteriocins are used in the foods in a ratio of the bacteriocin from LLA 2.0 and from LLA 1.2 in a ratio of 1 to 25 and 25 to 1 by weight. Preferably the ratio is 1 to 20 and 1 to 25 by weight of LLA 2.0 to LLA 1.2. The composition can be supplemented with various food grade fillers, such as starch, dextrose and the like to provide bulk.

SPECIFIC DESCRIPTION

The method for producing the preferred transconjugant strain of *Lactococcus lactis* producing two (2) bacteriocins is described hereinafter in Example 1. Conjugation was used since the plasmid transferred was too large for transformation or transduction. The plasmid can be reduced in size to accomplish DNA transfer by these latter methods; however conjugation is the easiest method. Example 1 shows the isolation of the transconjugant strain and the testing of the strain. Example 2 shows the use of the transconjugant strain in various foods.

EXAMPLE 1

Conjugative transfer of pSRQ400

The object of this Example 1 was to establish that (1) the resident plasmid pSRQ400 (69 Kb) encoding for lactose fermentation and bacteriocin production (LL-2+), could be introduced into another closely-related strain; (2) the transfer of pSRQ400 from *Lactococcus lactis* LLA 2.0 would be accomplished by conjugation (mating). The recipient is (a) insensitive to bacteriocins produced by LLA2.0; (b) is not inhibitory to LLA 2.0; (c) has antibiotic markers to select against the donor LLA 2.0; (d) is lactose negative (Lac−), so that transfer of pSRQ 400 can be easily followed; and (e) is a related strain (i.e.) within the same species or genus.

The strain used was *Lactococcus lactis* LLA 1.0, which could be passed through suitable gradations of desired antibiotics to obtain a spontaneous resistant mutant. On testing against LLA 2.0, it was found that the strain was insensitive to bacteriocins (LL-2A and LL-2B) produced by LLA 2.0. Also LLA 2.0 was not inhibited by LLA-1, which produced a bacteriocin called LL-1. Additionally, strain LLA-1 was lactose negative (Lac−). Because of these favorable traits LLA-1 was chosen as a recipient.

It was important at the outset to establish suitable screening procedures other than Lac+ phenotype to select for and confirm presumptive transconjugants. Other distinguishing characteristics between LLA-1 and LLA-2 had to be established. To achieve this end, a two-pronged approach was used.

(1) Screen LLA-1.0 and LLA-2.0 against a previously isolated phage, which was virulent for LLA 1.0. Screening showed that phage 11a-1, was specific for LLA-1.0 and did not infect LLA 2.0.

(2) Screen LLA-1.0 and LLA-2.0 against several possible indicators and find out if LLA-2.0 inhibited a strain that is not inhibited by LLA 1.0. Earlier work had shown that colonies of LLA-2.0 inhibited *Lactobacillus casei* 842 (NRRL-B-15972), while LLA 1.0 failed to show a similar inhibition. These characteristics could be used for non-selective marker analysis of possible transconjugants.

To further facilitate easy screening of Lac+ colonies appearing on selective agar plating of mating mixtures, it was decided to select a spontaneous mutant of LLA-1.0 resistant to these drugs.

| Selection of Str$^r$ derivative of LLA 1.0 | | | | |
|---|---|---|---|---|
| [Str]/ml | [Str]/5 ml | ml BMG | Str soln | Total vol |
| 0 | 0 | 5.0 | 0.0 | 5.0 |
| 5 | 25 | 4.75 | 0.25 (D) | 5.0 |
| 20 | 100 | 4.9 | 0.1 (C) | 5.0 |

-continued

| Selection of Str$^r$ derivative of LLA 1.0 | | | | |
|---|---|---|---|---|
| [Str]/ml | [Str]/5 ml | ml BMG | Str soln | Total vol |
| 50 | 250 | 4.75 | 0.25 (C) | 5.0 |
| 100 | 500 | 4.50 | 0.50 (C) | 5.0 |
| 500 | 2500 | 4.75 | 0.25 (B) | 5.0 |
| 1000 | 5000 | 4.50 | 0.50 (B) | 5.0 |
| 1500 | 7500 | 4.25 | 0.75 (B) | 5.0 |
| 2000 | 10000 | 4.00 | 1.00 (B) | 5.0 |

Make up stock sol. = 100,000 µg/ml (Soln. A) Filter sterilize. BMG = Basal Medium with Glucose.
1/10 dil A = 10,000 µg/ml (Soln. B) Use sterile distilled water for dilution.
1/10 dil B = 1,000 µg/ml (Soln. C).
1/10 dil C = 100 µg/ml (Soln. D).
str = Streptomycin Culture LLA-1.0 was step-wise transferred through these solutions and a resistant isolate (Str$^{2000}$) was purified and frozen. It was given the designation LLA 1.1. This strain was then used to develop a double-drug resistant mutant by exposure to fusidic acid. The isolated LLA 1.1 was sensitive to phage 11a-1.

To get a Fus$^r$ marker on LLA 1.1, Basal medium with glucose (BMG) agar was dispersed in 20 ml volumes into sterile screw-cap tubes.

5 mg of fusidic acid was weighed out, and dissolved in 5.0 ml methanol to give 1 mg (1000 µg)/ml-Soln A, it was diluted 1/10 to give Soln. B.

| [Fusidic]/ml | [Fusidic]/20 ml | ml Fusidic Stock |
|---|---|---|
| 1 µg | 20 µg | 0.2 ml of B |
| 5 µg | 100 µg | 0.1 ml of A |
| 10 µg | 200 µg | 0.2 ml of A |
| 20 µg | 400 µg | 0.4 ml of A |

Agar mixed with the drug was poured into sterile petri plates and allowed to solidify. The plates were dried of the surface moisture.

One tenth ml (0.1 ml) of an 18 hour culture of LLA 1.1 in BMG broth was spread on plates containing 1 µg/ml and 5 µg/ml fusidic acid. Colonies appearing on one of these plates were streaked onto plates containing higher concentration of the drug. By such a procedure a derivative resistant to 20 µg/ml of fusidic acid was obtained. This derivative was designated as LLA 1.2.

The strategy was to plate the mating mixtures on basal medium with lactose, bromocresol purple a pH indicator (BCP) and streptomycin. Lac+ colonies from mating plates were screened on Fus$^{10}$ plates to select for transconjugants.

Microorganisms: The spontaneous streptomycin- and fusidic acid-resistant, lactose-negative, plasmid-free, potent bacteriocin-producing *Lactococcus lactis* subsp. *lactis* strain designated as LLA 1.2 was used as the recipient in mating experiments. This strain produced a nisin-like bacteriocin. The donor was another strain of *Lactococcus lactis* subsp. *lactis* designated as LLA 2.0. The donor strain, LLA 2.0, produced two related bacteriocins, one of which was believed to be a degradation product of the other. Strain LLA 2.0 contained the single plasmid (pSRQ400) 69.0 Kb in size. Curing of this plasmid resulted in the loss of lactose-fermenting ability and bacteriocin production by LLA 2.0. Strain LLA 1.2 had no inhibitory action against LLA 2.0 and vice versa. Furthermore, colonies of LLA 2.0 were very inhibitory to *Lactobacillus casei* subsp. *casei* 842, while LLA 1.2 had no effect against this lactobacilli. *Lactobacillus casei* can be contaminants in foods or may be added to control molds.

A specific bacteriophage, designated 11a-1, which was virulent for LLA 1.2, but was inactive against LLA 2.0, was used to test for authentic transconjugants in mating experiments. Activity against *Lactobacillus casei* subsp. *casei* 842 was an additional test used in the selection of transconjugants. The microorganisms used and their characteristics are listed in Table 1.

TABLE 1

| Microorganisms and Phages Used. | | | | |
|---|---|---|---|---|
| Bacteria Phage | Strain Identity | Characteristics | Plasmid(s) | Comments |
| *Lactococcus lactis* subsp. *lactis* | | | | |
| | LLA 1.2 | Str$^r$, Fus$^r$, LL-1$^+$ Lac$^-$,LL-2$^-$ | None | Sensitive to phage 11a-1 |
| | LLA 1.2 (pGK41) | Str$^r$Fus$^r$, Ery$^r$ LL-1$^+$ Lac$^-$ LL-2$^-$ | pGK41$^a$ | Recipient sensitive to phage 11a-1 |
| | LLA 2.0 | Str$^s$, Fus$^s$, Er$^s$ LL-1$^-$ Lac$^+$ LL-2$^+$ | pSRQ 400$^b$ | Donor resistant to phage 11a-1 sensitive to phage 11a-1 |
| | LLA 1.2 (pGK41) T1 | Str$^r$, Fus$^r$, Ery$^r$ LL-1$^+$, LL-2$^+$ | pGK41$^a$ | Transconjugant sensitive to phage 11a-1 |
| | LLA 1.2 (pGK 41) T2 | Str$^r$, Fus$^r$, Ery$^r$ LL-1$^+$, LL-2$^+$ | pGK41$^a$ | Transconjugant sensitive to phage 11a-1 |
| *Lactobacillus casei* subsp. *casei* | | | | |
| | 842 | — | — | Indicator strain for Bac$^+$ colonies of LLA 2.0 and the transconjugants |
| *Pediococcus pentosaceus* | | | | |
| | FBB63 | — | — | General indicator for |

TABLE 1-continued

Microorganisms and Phages Used.

| Bacteria Phage | Strain Identity | Characteristics | Plasmid(s) | Comments |
|---|---|---|---|---|
| | | | | bacteriocins LL-1 and LL-2 |
| Phage | 11a-1 | — | — | Virulent for LLA 1.2, LLA 1.2 (pGK41), and transconjugants |

$Str^r$ - Streptomycin resistant; $Str^s$ - Streptomycin sensitive; $Fus^r$ - Fusidic acid resistant; $Fus^s$ - Fusidic acid sensitive; $Lac^+$ - Lactose positive; La - Lactose negative; $Ery^r$ - Erythromycin resistant; $Ery^s$ - Erythromycin sensitive;
$LL-1^+$ - Positive for production of bacteriocin LL-1; $LL-1^-$ - Negative for production of bacteriocin LL-2; $LL-2^-$ - Negative for production of composite bacteriocin LL-2.
$^a$pGK41: Gift from Dr. Jan Kok, University of Groningen, Netherlands.
$^b$pSRQ400: Patent Application 07/721,774
$^c$LLA 1.2 (pGK 4I) T1: Laboratory designation - Strain 302.

Media: Strain LLA 1.2 as routinely propagated in Basal Medium with glucose (BMG). Strain LLA 2.0 was cultured in Basal Medium with lactose (BML). The compositions of these media are described by Gonzalez and Kunka (Gonzalez, C. F. and B. S. Kunka., Appl. Environ. Microbiol. 46:81–89 (1983)). For solid media 1.5% agar was added to the respective broths. For selective plating of mating mixtures, BML-agar containing 0.008% bromocresol purple (BCP) as a pH indicator, and 1000 micrograms/ml streptomycin as selective agent was used. Lactose-positive colonies on BML(BCP)-$Str^{1000}$ plates were counter selected on BML(BCP)-$Fus^{10}$ plates to eliminate spontaneous $Str^r$ mutants of the donor. To test for phage-sensitivity a soft-agar overlay, seeded with the isolate was spotted with a high titer lysate of phage 11a-1. The media used for this test were solid and semisolid BMG agar fortified with 0.02% calcium chloride.

Bacteriocin Assay: Titer of bacteriocin in cell-free supernatants of cultures was determined on supernatants passed through 0.45 μm filter. The indicator used was *Pediococcus pentosaceus* FBB63C. Filtered supernatants and two-fold serial dilutions of the filtrates were spotted at 5 microliter volumes on moisture-free MRS-soft agar overlays of the indicator as described by Gonzalez and Kunka (Gonzalez., C. F. and B. S. Kunka, Appl. Environ. Microbiol. 53:2534–2538 (1987)). One activity unit (AU) is defined as the reciprocal of the highest dilution yielding a definite inhibition zone on the indicator lawn.

For demonstrating bacteriocin-production by colonies, individual colonies were transferred to moisture-free surface of buffered MRS-agar plates (MRS agar containing 1.9% of sodium β-glycerophosphate) with sterile toothpicks such that colonial growth from the transfers measured 1–2 mm in diameter. The transfers were made such that the developing colonies were separated from one another by at least 2 cm. After colonies developed, a layer of soft MRS-agar seeded with *Lactobacillus casei* subsp. *casei* 842 was poured. After incubating overnight at 35° C., plates were examined for inhibition of the indicator. A wide zone ($\geq 1$ cm) of clearing with crisp margins was scored positive for bacteriocin production.

Culture Mating Procedure: Agar surface mating procedure was used. The mating mixtures (Donor to Recipient ratio of 1:2 and 1:4.) and donor and recipient controls were spread on the surface of BMG-agar. A set of five plates for each experimental variable was used. Each plate was spread with 0.2 ml of the sample. Plates were incubated overnight at 32° C., and the cells were harvested by washing the agar surface with sterile phosphate buffer, pH 7.0, using 2.0 ml per plate. The total of approximately 10 ml. per sample from each set of five plates were pooled together, and the cells sedimented by centrifugation. After washing with 10 ml of phosphate buffer, the cells were resuspended in 1.1 ml buffer. The cells were then spread on five BML(BCP)-$Str^{1000}$ plates at 0.2 ml per plate. Plates were incubated in a Gas Pak Jar with the hydrogen-carbon dioxide generating pouch at 32° C. for 48 hours. At the end of the incubation period, the plates were examined.

Colony Screening: All lactose-positive, yellow colonies from the plates containing mating mixtures were short-streaked on BML(BCP)-$Fus^{10}$ plates to select against spontaneous $Str^r$ donor colonies. Presumptive transconjugants from the BML(BCP)-$Fus^{10}$ plates were screened for inhibitory activity against *L. casei* subsp. *casei* 842. Those exhibiting antagonistic activity, were streaked for single colony isolation (purification step) and retested for activity against strain 842. Colonies positive for antagonistic activity were tested for sensitivity to phage 11a-1. Colonies that were sensitive to the phage were grown in broth and stocked.

Plasmid DNA Isolation and Electrophoresis: Procedures described by Gonzalez and Kunka (Gonzalez, C. F. and B. S. Kunka, App. Environ. Microbiol. 46:81–89 (1983)) were used for the propagation of cells, cell-lysis, plasmid DNA isolation, electrophoretic separation and eithidium bromide staining of gels.

Purification of bacteriocin activity of transconjugant LLA 1.2 (pGK41) T1 (Lab designation 302):

Two liters of MRS broth (Difco, Detroit, Mich.) were inoculated at 1% with an 8 hour old culture of strain 302 (propagated in MRS broth) and were grown statically at 32° C. for 24 hours. Cells were removed by centrifugation at $16,300 \times g$ for 15 minutes at 4° C. The supernatant was filtered using a Minitan tangential filtration apparatus (Millipore, Bedford, Mass.) equipped with a 0.2 μm pore size polyvinylidene difluoride (PVDF) membrane. Bacteriocin production was assayed as previously described.

Filtrate from tangential filtration was concentrated approximately 6-fold using a spiral-wound cellulose-based S1Y3 ultrafiltration cartridge with a 1 ft$^2$ surface area and a 3000 dalton molecular weight cutoff (Amicon, Danvers, Mass.). Concentration was performed at 4° C. using a peristaltic pump (Cole-Parmer, Chicago, Ill.) to maintain a 20 lb/in² in differential across the membrane.

A 350 ml aliquot of concentrated supernatant was applied to a 10 cm×20 cm column (1.57 liters) of DEAE-650M anion exchange resin (Toso-Haas, Philadelphia, Pa.) equilibrated with 0.1M sodium acetate buffer, pH 4.0 at a flow rate of 110 ml/min. Absorbance of the eluent at 280 nanometers was monitored and eluent was collected from the first increase from baseline absorbance until baseline absorbance was again reached. The eluent volume was 3150 ml and the activity was 1600 AU/ml.

The entire volume of eluent from anion exchange chromatography was applied to a 10 cm×35 cm column (2.75 liters) of CM-650M cation exchange resin (Toso-Haas, Philadelphia, Pa.) which had been equilibrated against 0.1M sodium acetate buffer, pH 4.0. Activity was eluted using the same buffer containing 1M sodium chloride at pH 4.0. Eluent was collected from the first increase in conductivity from baseline conductivity (0.159 micro Siemans). Collection was terminated when absorbance at 280 nanometers returned to baseline absorbance. The eluent volume was 2000 ml and the activity was 400 units/ml.

The eluent from cation exchange chromatography was concentrated approximately 10-fold by ultrafiltration using an S1Y3 cartridge (Amicon Danvets, Mass.) until 100 ml remained. Sodium chloride content was then reduced approximately 125-fold by diafiltering three times with 400 ml deionized water and then concentrating to about 100 ml again. The cartridge was emptied and then washed with 100 ml deionized water. The concentrate was combined with the wash solution to obtain 230 ml bacteriocin with 3200 AU/ml activity.

Volume of the bacteriocin concentrate was further reduced using vacuum centrifugation (Savant, Farmingdale, N.Y.) until 16 ml remained with an activity of 64000 AU/ml. Aliquots of this concentrate were applied to a 2.5 cm×25 cm ODS column (Vydac, Hisperia, Calif.) equilibrated with 0.1% trifluoroacetic acid (TFA) in water. Activity was eluted using a gradient which typically used a linear change over 30 minutes from 20% to 40% acetonitrile (AcCN) containing 0.1% trifluoroacetic acid. A flow rate of 10 ml/min was used. Fractions were collected at 0.5 minute intervals and activity was located in the chromatogram by directly spotting 5 μl from each fraction onto an FBB63C indicator plate. Protein elution was monitored using a UV detector at 230 nanometers wavelength.

Characterization of bacteriocins: Comparisons were done of the activities of purified LL-1, LL-2A and LL-2B from the parent strains and the isolated 302A and 302B from the transconjugant strain. These comparisons were done on a 0.45 cm×25 cm $C_{18}$ analytical column (Vydac, Hisperia, Calif.).

RESULTS

Initial mating experiments revealed that the donor produced too many $Str^r$ colonies and, because of this, it was very difficult to select colonies for screening. To avoid this problem, an erythromycin-resistance marker ($Ery^r$) was introduced into the donor by electroporating the shuttle vector pGK41. In later mating experiments, selective plating of control and mating mixtures were made on BML(BCP)-$Str^{1000}Ery^5$ plates. On these plates no breakthrough of donor colonies was seen.

Mating mixtures plated on the erythromycin-containing agar produced very weakly lactose-positive ($Lac^+$) colonies. All such colonies were screened on fusidic acid-containing medium and colonies showing ready growth on that medium were checked for activity against strain 842. Those that were positive for inhibition against strain 842 were tested for susceptibility to the specific phage.

Two colonies satisfied all the screening criteria. This represented a transfer frequency of $2.0 \times 10^{-9}$ per donor cell input, as shown in Table 2.

| Donor | Recipient | Transfer Frequency | Transconjugants |
|---|---|---|---|
| LLA 2.0 | LLA 1.2 | $2.0 \times 10^9$ | LLA 1.2 (pGK 42) T1[a] |
|  | (pGK 41) |  | LLA 1.2 (pGK 41) T2 |

[a]Laboratory designation 302.

The two isolates, however, lost their $Lac^+$ phenotype but retained the inhibitory activity against strain 842 during the screening process. Examination of their plasmid content showed the lack of any plasmid in both the strains.

Further testing of the transconjugants consisted of the analysis of the bacteriocin(s) produced by one of the strains. Purification of bacteriocin(s) produced by one of the transconjugants, LLA 1.2 (pGK41) T1 (laboratory designation 302) was done primarily to verify the presence of two distinct bacteriocins. The strains appeared to be identical.

Elution times of purified LL-1, LL-2A and LL-2B from the parent strains were determined separately. A 30 minute 20–40% AcCN gradient elutes LL-2A at 26.5', LL-2B at 37' and LL-1 at 35'. The purified 302 concentrate using the 20–40% AcCN gradient revealed two areas of activity, one at 26.5' and the other between 38 and 40'. Only the second of these areas was associated with a defined peak. The active fractions were isolated and named 302A and 302B, respectively. Further runs were completed using this method. At completion, five separate HPLC runs were performed, each of the heart cuts (determined by association with a peak) were brought up to 0.5 ml with $dH_2O$, titered and analyzed for protein concentration. These pure fractions were stored at −20° C.

To compare the various purified bacteriocin entities obtained through purification, mixtures were made combining 302B with equivalent amounts of LL-1 or LL-2B to determine which of the bacteriocins would co-elute with 302B. Previously, it had been found that LL-1 and LL-2B, though eluting within a very close range, resolved as two peaks using a 0–45% AcCN gradient. Equal amounts of LL-2B and 302B also showed elution of two peaks indicating that two separate bacteriocins were present. In contrast, equal amounts of LL-1 and 302B eluted only a single peak. Thus, 302B appears to be identical to LL-1. In a similar manner, 302A was compared to LL-2A. On an analytical scale (0–45% AcCN, 30') 302A and LL-2A elute at 27.1'. The results are shown in Tables 3 and 4.

TABLE 3

Summary of Purification of bacteriocins from *Lactococcus lactis* subsp. *lactis* strain 302 [LLA 1.2 (pGK41)T1].

| Step | Volume (ml) | Titer Au/ml | Total Activity Au | Yield Step % | Yield Total % | Specific Activity Au/mg protein |
|---|---|---|---|---|---|---|
| Crude | 2000 | 800+ | 1.6M | | | |
| Amicon | 350 | 1600+ | 560K | | 35 | |
| IEX | 2000 | 400+ | 800K | 143 | 50 | |
| Amicon | 232 | 3200 | 742K | 93 | 46 | |
| Speed Vac | 16 | 64000 | 1024K | 138 | 64 | |
| HPLC: | | | | | | |
| 302A | | | | | | |
| 26.5' | 0.5 | 6400 | 3200 | 3 | 0.2 | 12.5K |
| 302B | | | | | | |
| 32.5' | 0.5 | 128K | 64K | 23 | 15 | 213K |
| 38.5' | 0.5 | 256K | 128K | | | 291K |

TABLE 4

Typical HPLC elution times of bacteriocins from strains LLA-1.2, LLA-2.0 and 302.

| Bacteriocin | 20–40% AcCN 30' | 0–45% AcCN 30' Analytical Scale |
|---|---|---|
| LL-2A | 26.5' | 27.7' |
| 302A | 26.5' | 27.1' |
| LL-2B | 37' | 31.5' |
| LL-1 | 35' | 31.1' |
| 302B | 38' | 31.1' |

Note:
Mixing equal amounts LL-1 and LL-2B yields two peaks.
Mixing equal amounts 302B and LL-1 yields a single peak.
Mixing equal amounts 302B and LL-2B yields two peaks.
Mixing equal amounts LL-2A and 302A yields a single peak.

The mating did result in expression of two different bacteriocin activities, one appearing to be LL-1 and the other comparable to LL-2A, the weaker of the two bacteriocins associated with LLA 2.0 bacteriocin production. Thus, the Bac+ genes from LLA 2.0 have been successfully integrated into the LLA 1.2 chromosome with partial phenotypic expression evident by production of the bacteriocin LL-2A.

The bacteriocin LL-2B was not detected in purified isolates from 302 medium. Purified LL-2B isolated from LLA 2.0 medium has a single peak in the HPLC chromatogram and will, over time, form a second entity which elutes at the same position as LL-2A. Purified LL-2A seems stable over time since it continues to appear as a single peak in the chromatogram. From these results the conclusion can be reached that LL-2A is related to LL-2B and that the relationship is such that either LL-2A is a product of irreversible alteration of the molecular structure of LL-2B, or that LL-2A represents a slowly forming but much more stable conformation of LL-2B. The presence of LL-2A in isolates of 302 medium is, therefore, interpreted as indirect evidence of the presence of the parent LL-2B protein at some prior point, even though it was not detected at the time of final analysis.

Inhibition of *Lactobacillus casei* 842 was tested using each of the purified bacteriocins LL-1, LL-2A, LL-2B, 302A and 302B. Previous tests with whole cells showed inhibition when the lines LLA 2.0 (produces LL-2) or 302 (produces LL-1 and LL-2) were present but not when the line LLA 1.2 (produces LL-1) was present. In contrast, on spotting 5 μl of 6400 AU/ml purified bacteriocin, LL-1, LL-2B, and 302B inhibited the growth of *L. casei* 842, while LL-2A and 302A did not. Evidently, the 302 cell line is more effective in its anti-bacterial activity toward *L. casei* 842 than the LLA 1.2 cell line. According to inhibition studies involving purified bacteriocins, only the LL-1 component of 302 cell bacteriocin production is active against *L. casei* 842. From this it was concluded that genetic modifications as a result of the mating experiment have increased the effectiveness of LL-1 mediated activity against *L. casei* 842 compared to LLA 1.2 cells. The results are shown in Table 5.

| Inhibition[a] by Whole cells | | Inhibition[a] by Purified Bacteriocins[b] | |
|---|---|---|---|
| LLA 1.2 | no | LL-1 | yes |
| LLA 2.0 | yes | LL-2A | no |
| | | LL-2B | yes |
| 302 | yes | 302A | no |
| | | 302B | yes |

[a]Inhibition of *Lactobacillus casei* strain 842.
[b]Bacteriocins adjusted to 6400 Au/ml titer.

EXAMPLE 2

The suppressive activity of *Lactococcus lactis* ssp. *lactis* NRRL-B-18422 against *Lactobacillus casei* 842 was tested in a sour cream dip system, which can also be extended to fermented milk-based salad dressings. This system was specifically chosen because the microorganisms in question could be used in these systems as supplementary shelf-life extending agents. *Lactobacillus casei* 842 has previously been shown to inhibit molds (U.S. Pat. No. 4,956,177) to King et al. This mold-inhibiting lactobacilli, however, can produce excessive amounts of lactic acid in milk-based dip and dressing mixtures and cause too much souring and phase-separation because of wheying-off.

Hence, there is a need for regulating acid-production and growth of *L. casei* 842 in such systems without affecting its mold-suppressing activity. Because the transconjugant NRRL-B-18422 inhibits *L. casei* 842, their interaction in a sour cream dip system was tested in this example.

Procedure: Fresh sour cream was purchased from the store. One hundred gram portions of the sour cream were weighed into four screw-cap jars. To each portion, 5.0 grams of "Ranch Flavor" spice mix were added and mixed thoroughly with a spatula. The jars were labeled 1, 2, 3 and 4. Jar 1 served as the control without any microbial additive. To jar 2, sufficient dilution of a fresh milk culture of *L. casei* 842 was added such that a count of $1 \times 10^5$ to $1 \times 10^6$ cfu/g was available. To jar 3, a dilution of a fresh culture of *Lactococcus lactis* ssp. *lactis* NRRL-B-18422 was added such that a count of $1 \times 10^3$ to $1 \times 10^4$ cfu/gm was present. To jar 4, *L. casei* 842 at the same level as in jar 2 and NRRL-B-18422 at the same level as in jar 3 were added as a mixture. All the jars were thoroughly mixed with four separate spatulas. The *L. casei* 842 strain used in this example contained a chromosomal Rifamycin-resistance marker. The transconjugant NRRL-B- 18422 contained an Erythromycin-resistance plasmid. The marked strains allowed selective enumeration of the two strains in the presence of other flora in the sour cream with spice mixture as well as in the mixture containing both strains, namely, as in jar 4.

Counts of the added bacteria were determined immediately after uniform incorporation. For counting NRRL-B-18422, APT-agar containing 5 micrograms/ml of Erythromycin was used. To count *L. casei*

842, MRS-agar with 200 micrograms/ml of Rifamycin was used. The samples were held at room temperature for a week, and examined every day for visual appearance, aroma and odor. At the end of the week, counts were made and the pH was measured.

Results:

| Jar No. | Counts: cfu/gm | | | |
|---|---|---|---|---|
| | Initial | | Final | |
| | 842 | 18422 | 842 | 18422 |
| 1 | — | — | — | — |
| 2 | $1 \times 10^6$ | — | $>1 \times 10^8$ | — |
| 3 | — | $3.7 \times 10^3$ | — | $3 \times 10^4$ |
| 4 | $1 \times 10^6$ | $4.1 \times 10^3$ | $>1 \times 10^6$ | $7 \times 10^2$ |

Visible Mold Growth:
Days at room temperature

| Jar. No. | 1 | 2 | 3 | 4 | 5 | 6 | 7 |
|---|---|---|---|---|---|---|---|
| 1 | — | — | — | + | ++ | ++ | +++ |
| 2 | — | — | — | — | — | — | — |
| 3 | — | — | — | + | ++ | ++ | +++ |
| 4 | — | — | — | — | — | — | — |

— = Negative; + = Slight; ++ = Large patches

Aroma and Odor:
Days at room temperature

| Jar No. | 1 | 2 | 3 | 4 | 5 | 6 | 7 |
|---|---|---|---|---|---|---|---|
| 1 | G | F | M | M | M | M | M |
| 2 | G | G | G | S | S | S+ | S+ |
| 3 | G | G | M | M | M | M | M |
| 4 | G | G | G | G | G | G | G |

G = Good, normal "ranch" odor and aroma
F = Flat, lack of acid odor and aroma
M = Moldy, musty odor
S = Sour smell
S+ = Extremely sour odor The pH of jars 1 and 3 were not taken at the end of 7 days because of visible mold growth. The pH of jar 2, which was excessively sour smelling, was 3.8. The pH of jar 4, which maintained the good "ranch" aroma, was 4.0.

Conclusions:

The addition of L. casei by itself controlled mold growth but resulted in excessive acid accumulation when the "Ranch Dip" was held at room temperature for 7 days. Without any additions or with only NRRL-B-18422, mold contamination from the spice mixture grew unchecked and affected the visual appearance, and imparted a moldy, musty odor to the dip. In the presence of NRRL-B-18422, L. casei 842 inhibited the mold from developing. At the same time, the inhibitory activity of the lactococci against the lactobacilli prevented the unrestricted increase in the number of the lactobacilli thus controlling accumulation of excessive lactic acid. The visual appearance, aroma and odor of jar 4 was normal.

It is intended that the foregoing description be only illustrative of the present invention and that the present invention be limited only by the hereinafter appended claims.

---

We claim:
1. A bacterial composition which comprises:
   (a) cells of a *Lactococcus lactis* NRRL-B-18535 and cells of *Lactococcus lactis* NRRL-B-18809 in amounts together which are sufficient to inhibit growth of *Lactococcus casei* NRRL-B-15972 in a food.
2. A biologically pure culture of *Lactococcus lactis* subspecies *lactis* having all the identifying characteristics of *Lactococcus lactis* subspecies *lactis*, NRRL-B-18922.

* * * * *

UNITED STATES PATENT AND TRADEMARK OFFICE
CERTIFICATE OF CORRECTION

PATENT NO. : 5,348,881

DATED : September 20, 1994

INVENTOR(S) : Ebenezer R. Vedamuthu, James T. Henderson, Peter A. Vandenbergh

It is certified that error appears in the above-indentified patent and that said Letters Patent is hereby corrected as shown below:

On the title page item [73], "Good" should be --Food--.

On the title page item [56], "Vadamuthu" should be --Vedamuthu--.

On the title page item [56], Geis Reference, "Bacteriocini" should be --Bacteriocin--.

Column 6, Table 1, line 5 under heading "Characteristics", "$Er^s$" should be --$Ery^s$--.

Column 6, Table 1, under heading "Comments", lines 9 and 10 should be deleted "sensitive to phage 11a-1".

Column 7, line 60, "($\geq$ 1cm)" should be --($\geq$ 1 cm)--.

Column 9, line 27, "Danvets" should be --Danvers--.

UNITED STATES PATENT AND TRADEMARK OFFICE
CERTIFICATE OF CORRECTION

PATENT NO. : 5,348,881

DATED : September 20, 1994

INVENTOR(S) : Ebenezer R. Vedamuthu, James T. Henderson, Peter A. Vandenbergh

It is certified that error appears in the above-indentified patent and that said Letters Patent is hereby corrected as shown below:

Column 10, line 12, the following should be inserted --Table 2. Frequency of transfer of $Bac^+$ phenotype between *Lactococcus lactis* subsp. *lactis* LLA 2.0 and *Lactococcus lactis* subsp. *lactis* LLA 1.2 (pGK 41)--.

Column 12, line 11, the following should be inserted --Table 5. Activity of cellular and purified bacteriocins from strains LLA 1.2, LLA 2.0 and 302.--.

Column 16, line 18, Claim 1, "*Lactococcus casei*" should be --*Lactobacillus casei*--

Signed and Sealed this

Tenth Day of January, 1995

Attest:

BRUCE LEHMAN

*Attesting Officer*          *Commissioner of Patents and Trademarks*